United States Patent
Wang et al.

(10) Patent No.: US 7,300,534 B2
(45) Date of Patent: Nov. 27, 2007

(54) BONDS BETWEEN METALS AND POLYMERS FOR MEDICAL DEVICES

(75) Inventors: Lixiao Wang, Long Lake, MN (US); Dachuan Yang, Hillsborough, NJ (US); Joe Randall, Maple Grove, MN (US); (Bruce) Yiqun Wang, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 555 days.

(21) Appl. No.: 10/050,476

(22) Filed: Jan. 15, 2002

(65) Prior Publication Data
US 2003/0135197 A1 Jul. 17, 2003

(51) Int. Cl.
C03B 29/00 (2006.01)
C01G 23/00 (2006.01)
A61M 29/00 (2006.01)

(52) U.S. Cl. .................. 156/89.14; 423/598; 604/103
(58) Field of Classification Search ........... 604/103, 604/103.01, 103.04, 523–524; 427/266, 427/387; 525/327.8; 423/598; 156/89.14; 264/102
See application file for complete search history.

(56) References Cited

U.S. PATENT DOCUMENTS

| | | | |
|---|---|---|---|
| 3,669,825 A * | 6/1972 | Hall et al. ................ 428/420 |
| 4,069,192 A * | 1/1978 | Monte et al. .............. 523/451 |
| 4,741,931 A * | 5/1988 | Lin et al. ................. 427/387 |
| 5,190,795 A * | 3/1993 | Culler ..................... 427/226 |
| 5,470,923 A * | 11/1995 | Krahnke et al. ........... 525/477 |
| 5,514,734 A * | 5/1996 | Maxfield et al. .......... 523/204 |
| 5,549,552 A * | 8/1996 | Peters et al. ............. 604/103.1 |
| 5,567,203 A | 10/1996 | Euteneuer et al. |
| 5,679,201 A | 10/1997 | Gardiner |
| 5,681,402 A * | 10/1997 | Ichinose et al. ........... 136/256 |
| 5,861,032 A | 1/1999 | Subramaniam |
| 5,921,958 A | 7/1999 | Ressemann et al. |
| 5,928,916 A | 7/1999 | Keogh |
| 5,962,563 A | 10/1999 | Forrestal et al. |
| 6,013,855 A | 1/2000 | McPherson et al. |
| 6,040,058 A | 3/2000 | Hostettler et al. |
| 6,093,463 A | 7/2000 | Thakrar |
| 6,458,867 B1 * | 10/2002 | Wang et al. ............... 523/105 |
| 6,730,064 B2 * | 5/2004 | Ragheb et al. ............ 604/265 |
| 2003/0133247 A1* | 7/2003 | Ajioka ..................... 361/211 |
| 2003/0161976 A1* | 8/2003 | Rea et al. ................. 428/35.7 |
| 2003/0165647 A1* | 9/2003 | Kaneko et al. ............ 428/36.3 |
| 2004/0079429 A1* | 4/2004 | Miller et al. .............. 138/123 |
| 2004/0139820 A1* | 7/2004 | Kodas et al. ............... 75/252 |
| 2004/0199109 A1* | 10/2004 | Wantink ................ 604/103.04 |

OTHER PUBLICATIONS

Plueddemann, "Coupling Agents," source unknown, vol. 4, dated on or before Jan. 15, 2002, pp. 284-298.

* cited by examiner

Primary Examiner—Kevin C. Sirmons
Assistant Examiner—Andrew Gilbert
(74) Attorney, Agent, or Firm—Crompton, Seager & Tufte, LLC

(57) ABSTRACT

Various coupling agents are disclosed to form lap joints between metallic and polymeric surfaces within catheters and other medical devices. The coupling agents disclosed in the present invention can be applied directly to a metallic surface, or the coupling agents may be incorporated within a polymeric material. In certain circumstances, the mere application of the coupling agent between the two dissimilar materials provides sufficient adhesive strength to form a fatigue-free lap joint bond. Alternative methods utilize coupling agents as primers for later thermal bonding and laser welding procedures that form lap joint bonds.

7 Claims, 2 Drawing Sheets

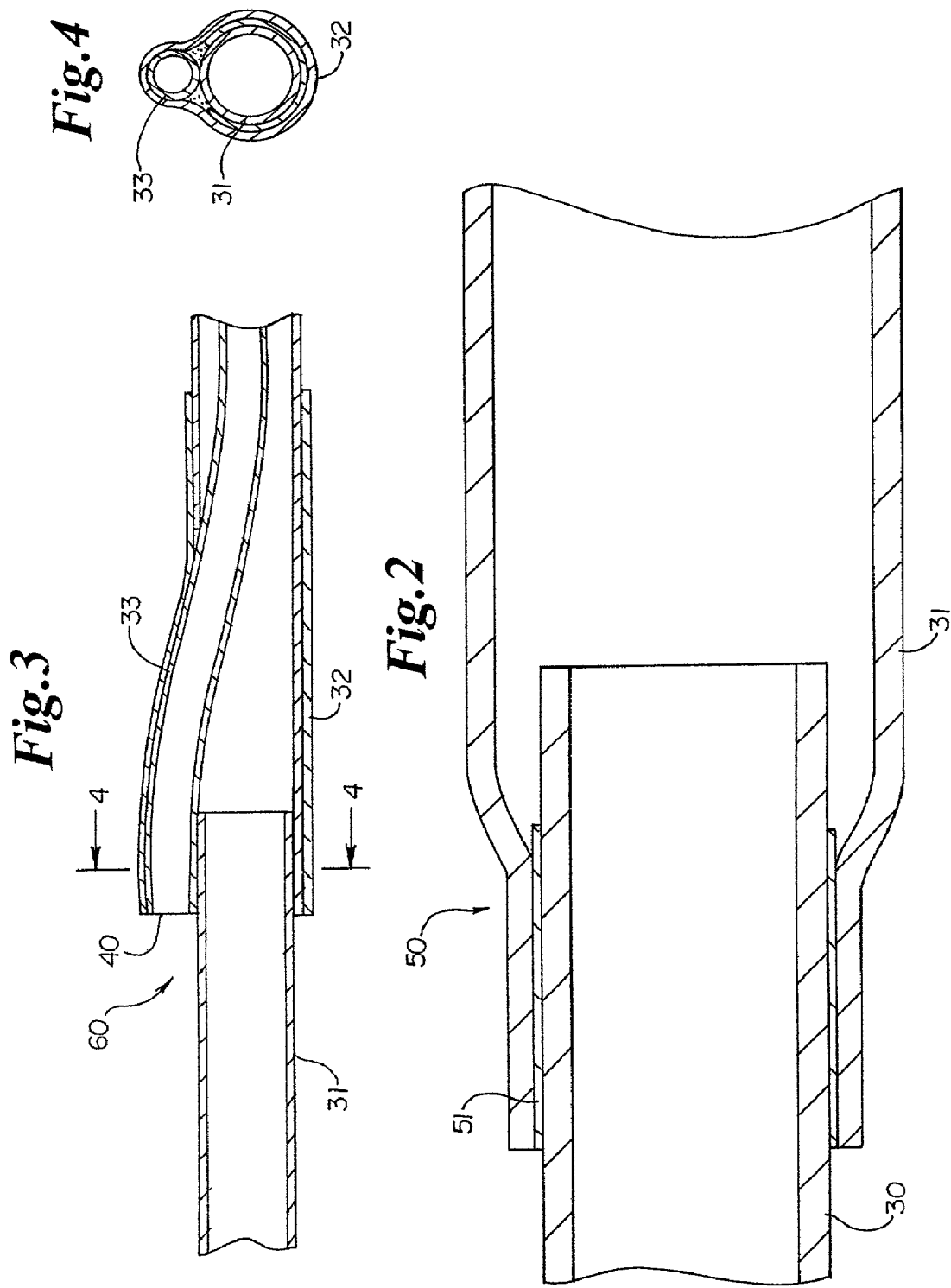

BONDS BETWEEN METALS AND POLYMERS FOR MEDICAL DEVICES

TECHNICAL FIELD

The present invention relates generally to the field of intravascular medical devices having a polymeric material disposed directly upon a metallic surface of the medical device. More specifically, the present invention relates to the use of a coupling agent to improve the physical properties, processing and performance of a bond formed between a metallic surface and a polymeric overlay in a catheter shaft, as well as other similar medical devices.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art, and typically involve the use of a balloon catheter with a guidewire, possibly in combination with other intravascular devices such as stents. A typical balloon catheter has an elongate shaft with a balloon attached proximate the distal end and a manifold assembly attached to the proximal end. In use, the balloon catheter is advanced over the guidewire such that the balloon is positioned adjacent a restriction in a diseased vessel. The balloon is then inflated, and the restriction in the vessel is opened.

There are three basic types of intravascular catheters for use in such procedures including fixed-wire (FW) catheters, over-the-wire (OTW) catheters and single-operator-exchange (SOE) catheters. The general construction and use of FW, OTW and SOE catheters are all well known in the art. An example of an OTW catheter may be found in commonly assigned U.S. Pat. No. 5,047,045 to Arney et al. An example of an SOE balloon catheter is disclosed in commonly assigned U.S. Pat. No. 5,156,594 to Keith.

The pushability and the trackability of a catheter are two performance characteristics essential to the success of intravascular catheters in medical procedures. Pushability refers to the catheter's ability to transmit force from the proximal end of the catheter to the distal end of the catheter. Trackability refers to the catheter's ability to navigate the tortuous vasculature of a patient. The trackability of a particular catheter design is analyzed in terms of the trackability of the distal portion of the catheter. The distal portion is the section of the catheter that must track the guidewire through the small tortuous vessels of a patient's vasculature. The size of the distal tip, the flexibility of the distal tip and the lumen diameter all influence the trackability of a catheter. Imparting more flexibility to the distal portion of a catheter, in particular, is found to improve catheter trackability. Moreover, increasing the flexibility within the distal tip improves handling and navigation over a guidewire.

Materials particularly suitable for enhancing the pushability of a catheter also decrease a catheter's trackability, and the converse. For example, if a catheter is comprised entirely of a flexible polymeric material, the catheter loses pushability and may be unable to drive the balloon to its proper position within a patient's vasculature. Likewise, if a catheter is comprised entirely of a rigid polymeric material, the catheter may be unable to navigate the tortuous pathways of a patient's vasculature. As a result, prior art catheter manufacturers have reached compromises in materials and construction in order to accommodate these two conflicting performance characteristics.

In efforts to accentuate both pushability and trackability within a single catheter design, manufacturers have experimented with various catheter materials. A specific example of such material selection is the use of hypotube tubing. The term "hypotube," as used herein, refers generally to a thin-walled, high-strength metallic tube having a lumen extending the length therein. The hypotube is preferably a stainless steel hypodermic tube that exhibits superior pushability characteristics.

Additionally, manufacturers have incorporated these various materials at particular locations on a catheter. Strategically positioning these materials along the length of a catheter frees manufacturers from the performance compromises associated with prior art catheters. For example, often the hypotube construction is incorporated within the proximal shaft region of a catheter, either entirely or in part, due to its superior pushability characteristics. Alternatively, a flexible polymeric material, such as high-density polyethylene, is incorporated within the distal shaft region of the same catheter.

An example of a catheter incorporating the enhanced pushability performance associated with a hypotube with the improved trackability of a flexible distal region is disclosed in U.S. Pat. No. 5,567,203, to Euteneuer, et al., the disclosure of which is incorporated herein by reference. In some embodiments, the Euteneuer et al. patent discloses an intravascular balloon catheter having a proximal hypotube shaft segment, a distal polymer shaft segment, a distally-mounted inflatable balloon segment, and a hollow tubular member having a proximal end connected to the distal end of the hypotube shaft segment such that the lumen of the hollow tubular member is in communication with the exterior of the balloon catheter, and the distal end of the hollow tubular member is connected to the distal end of the balloon.

The above-described materials that, in combination, accentuate medical device performance also tend to adhere poorly to one another. Bonds formed between these dissimilar materials are often exposed to stresses. Improvement in the bond between metal and polymeric components of a catheter shaft is desirable.

SUMMARY OF THE INVENTION

The present invention overcomes many of the disadvantages of the prior art by providing an improved lap joint between metallic and polymeric surfaces of catheters and other similar intravascular medical devices. The present invention also provides various coupling agents to increase the bonding affinity between otherwise dissimilar materials of a lap joint in an intravascular catheter.

The present invention discloses specific families of coupling agents that are particularly suitable for bonding polymeric materials to the metallic components or frameworks of medical devices. In particular, the present invention discloses specific coupling agents capable of forming a fatigue-free catheter lap joint at room temperature. The present invention additionally discloses coupling agents that are particularly suited for methods of lap joint manufacturing utilizing thermal bonding and/or laser welding.

In another embodiment of the present invention, a process is disclosed for improving bonding in lap joints between metallic surfaces and polymeric surfaces in catheter shafts. In particular, coupling agents are disclosed for the process that may be applied directly to a metallic surface, or alternatively, the coupling agents may be incorporated within a polymeric material that is later extruded over the metallic surface of the medical device.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 2 is a partial cross-sectional view of a portion of the catheter assembly of FIG. 1 having a lap joint between a metallic tubular member and a polymeric tubular overlay;

FIG. 3 is a partial cross-sectional view of a single operator exchange guidewire port joint of the catheter of FIG. 1 including a metallic tubular member joined with two polymeric members; and FIG. 4 is a cross-sectional view at 4-4 of FIG. 3 depicting further details of the joint.

DETAILED DESCRIPTION OF THE PREFERRED EMBODIMENTS

Figure 1:
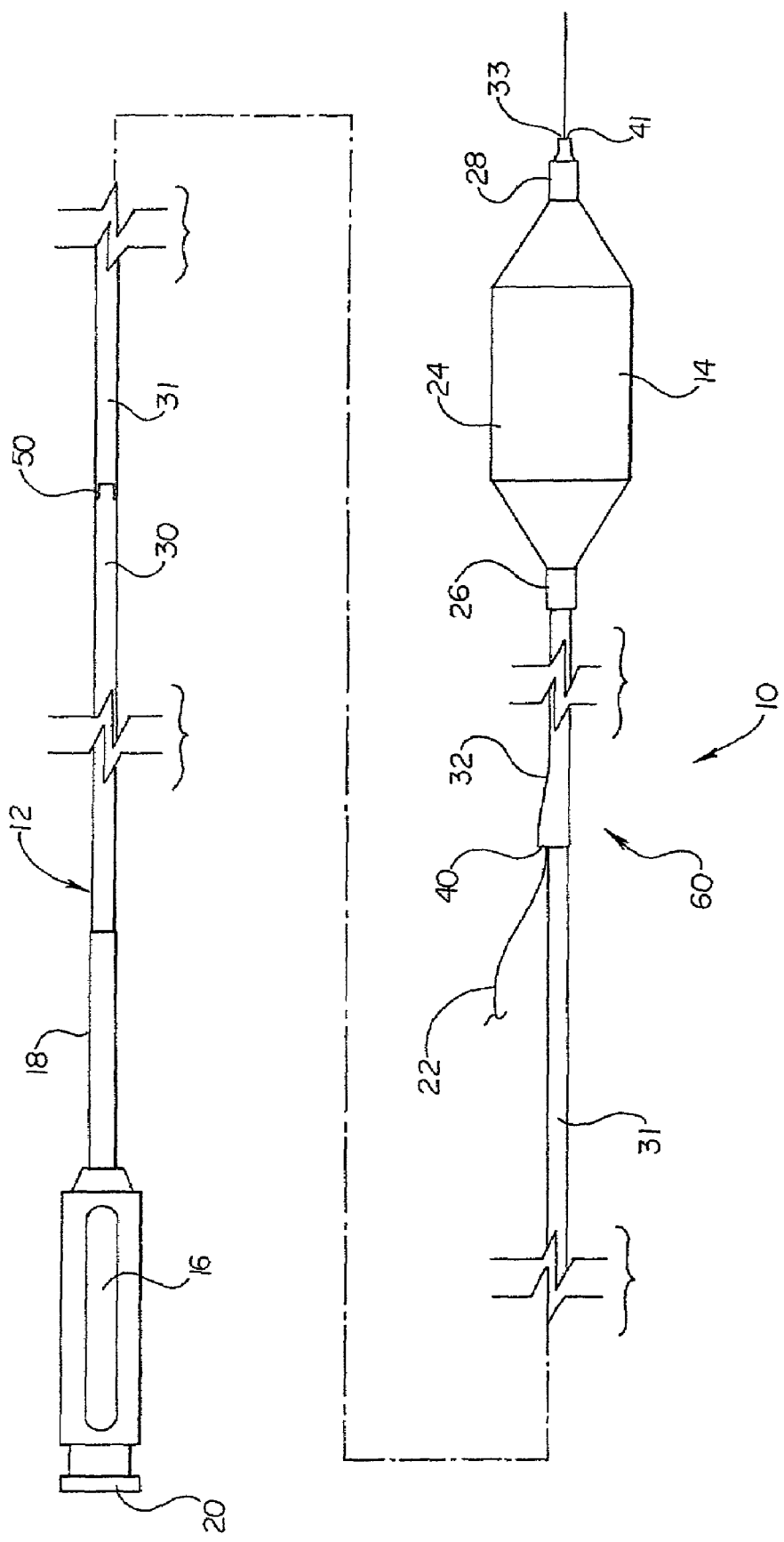
FIG. 1 is a partial plan view of a catheter assembly depicting potential locations for lap joints in accordance with the present invention.

The following detailed description should be read with reference to the drawings, in which like elements in different drawings are numbered identically. The drawings, which are not necessarily to scale, depict selected embodiments and are not intended to limit the scope of the invention. Examples of construction, materials, dimensions, and manufacturing processes are provided for selected elements. All other elements employ that which is known to those skilled in the field of the invention. Those skilled in the art will recognize that many of the examples provided have suitable alternatives that may be utilized.

Referring now to the drawings, FIG. 1 is a schematic plan view of a single operator exchange (SOE) dilation balloon catheter 10, which is representative of one type of catheter that can incorporate bonds of the present invention. Other intravascular catheter embodiments are additionally suitable without deviating from the spirit and scope of the present invention. For example, intravascular catheters suitable for incorporating the present invention include fixed-wire (FW) catheters and over-the-wire (OTW) catheters.

The balloon catheter 10 includes a shaft assembly 12 and a balloon assembly 14 connected proximate the distal end of shaft assembly 12. The proximal end of the shaft assembly 12 extends into a manifold assembly 16 adhesively bonded to the shaft assembly 12. A manifold port 20 extends from the manifold assembly 16 for attaching and fluidly connecting ancillary apparatus to a lumen extending through the balloon catheter 10. Multiple manifold ports can be included terminating into either a common lumen or a dedicated lumen extending within the shaft assembly 12 (e.g., a guidewire lumen in an OTW catheter). Functionally, the manifold assembly 16 additionally provides a convenient place for a physician to apply longitudinal or rotational forces in order to manipulate the catheter 10 during a medical procedure.

Referring specifically to FIG. 1, the manifold assembly 16 illustrated includes a luer type manifold port 20. In alternative embodiments, the union between the manifold assembly 16 and ancillary medical devices (not shown) is completed using alternative connectors. Alternative connecting mechanisms between the manifold assembly 16 and ancillary medical devices, being known in the art, are also incorporated as within the spirit and scope of the present invention.

A strain relief 18 is fit to the manifold assembly 16, and the shaft assembly 12 extends into the manifold assembly 16 through the strain relief 18. In specific embodiments, a proximal corewire (not shown) can be securely attached within the manifold assembly 16. The proximal corewire is generally a stainless steel wire member that provides additional stiffness and kink resistance throughout the proximal region of the catheter 10. This added proximal support again aids in the pushability of the catheter 10 to traverse the intravascular anatomy of a patient.

The shaft assembly 12 depicted in FIG. 1 includes multiple outer tubular members to illustrate exemplary uses of metal-to-polymer lap joints of the present invention. It is recognized that in preferred embodiments, not all illustrated joints are used in a single embodiment. The outer tubular members include a proximal segment 30, an intermediate segment 31 and a distal segment 32. In preferred embodiments of an SOE catheter, an inner tubular member 33 extends coaxially with a portion of the outer tubular member from a guidewire port 40 to the distal end 41 of the catheter to define an annular inflation lumen therebetween. In one embodiment, the outer tubular member segments 30, 31, 32 surrounding the inner tubular member 33 have an outer diameter ranging from about 0.040 inches to about 0.045 inches, with a wall thickness ranging from about 0.0028 inches to about 0.0044 inches. Materials used to form the outer tubular member segments 30, 31, 32 may vary depending upon the stiffness desired for the particular portion of shaft assembly 12. When the use of polymeric materials is desired, nylon and similar polyamides such as DURETHAN® (available from Bayer) are particularly suitable for obtaining rigid outer tubular members. Other suitable polymeric materials forming a rigid outer tubular segment include, but are not limited to, polyetheretherketone (PEEK), polyimide (PI), and polyetherimide (PEI). Additional rigidity within a polymeric material may be imparted to an outer tubular member segment by incorporating a braid or other support member on or within the tubular member.

As discussed in detail below, in preferred embodiments, at least one of the outer tubular member segments 30, 31 may comprise a metallic tube or hypotube. In these embodiments, the hypotube can be utilized as the outer tubular member segment 30, 31 in the more proximal regions of the catheter 10 to provide stiffness and torqueability. The hypotube segment can then be bonded to a more flexible polymeric outer tubular member 31, 32 at a distal region of the catheter shaft 12, later discussed in detail with respect to FIG. 2 and FIG. 3.

The inner tubular member 33 defines a guidewire lumen, which provides a passage for at least one guidewire 22. The inner tubular member 33 is generally made of a polymeric material such as a polyethylene, for example Marlex HDPE. In alternative embodiments, the inner tubular member 32 can be made of a lubricious material such as polytetrafluoroethylene (PTFE) or other suitable polymer. At the proximal end of the inner tubular member 33, the inner tubular member 33 has an outside diameter ranging from 0.024 inches to 0.026 inches. The inner diameter of the inner tubular member 33 measures approximately 0.018 inches to 0.0195 inches. The outside diameter-to-wall thickness ratio is preferably sufficiently small to reduce the likelihood that the shaft assembly 12, and more specifically the inner tubular member 33, will kink.

At the distal end of the shaft assembly 12 is a balloon assembly 14. The balloon assembly 14 includes an expansible balloon 24 having a proximal balloon waist 26 and a distal balloon waist 28. The proximal balloon waist 26 adheres the expansible balloon 24 to the distal tubular segment 32 near its distal end by means of an adhesive, or alternatively, by thermally bonding, including RF bonding, laser bonding and other suitable thermal bonding techniques. The distal balloon waist 28 similarly adheres the expansible balloon 24 to the inner tubular member 33 near its distal end by means of an adhesive bond or a thermal bond. This particular balloon assembly 14 arrangement allows the expansible balloon 24 to be in fluid communication with the inflation lumen defined by the outer tubular member segments 30, 31, 32.

As discussed in detail above, the proximal region and the distal region of a catheter 10 are functionally different and, therefore, preferably possess differing structural attributes to enhance their particular functionality. The distal region of a catheter 10 is designed for flexibility. Intravascular procedures often require a catheter 10 to track through a tortuous pathway to a desired location within a patient's body. Navigation through the vascular system requires the distal tip, as well as the remaining sections of the catheter 10, to bend and twist to complement the tortuous vasculature. The proximal region of a catheter 10, on the other hand, must provide sufficient longitudinal and axial strength to advance the entire distal region of the catheter 10 within a patient's anatomy. A joint is required at locations where materials of differing properties are utilized in the catheter shaft. FIG. 1 depicts two exemplary locations and types of joints which may be utilized. The first depicted joint is a lap joint 50 between proximal segment 30 and intermediate segment 31. In this embodiment, proximal segment 30 is preferably a metallic hypotube and intermediate segment 31 is a polymeric tubular member having greater flexibility. The lap joint 50 is depicted in greater detail in FIG. 2 and discussed below. The second exemplary joint depicted in FIG. 1 is lap joint 60 which is located at the proximal guidewire port 40 of the SOE catheter design. In this embodiment, intermediate tubular member 31 is preferably a metallic hypotube which forms a lap joint with distal outer tubular segment 32 and inner tubular member 40. This joint is shown in greater detail in FIGS. 3 and 4 and discussed in detail below. It should be recognized that the number of tubular segments incorporated into the outer tubular member can be varied for particular applications. The proximal member 30 and intermediate member 31 may also be combined to include a single hypotube member eliminating joint 50 and only including the port joint 60 discussed below.

Refer now to FIG. 2, where a cross-sectional view of joint 50 between proximal segment 30 and intermediate segment 31 of the outer tubular shaft of the catheter assembly 10 of FIG. 1 is shown in detail. The joint 50 of catheter 10 transitions between the proximal segment 30 and the intermediate segment 31 of the shaft assembly 12. Transitioning between regions reduces kinking and increases force transference between the two regions.

The joint 50 of catheter 10 depicted in FIG. 2 shows a proximal portion of intermediate segment 31 overlying and affixed to a distal portion of the proximal segment 30 via a coupling agent 51 (depicted in exaggerated thickness as a separate layer). The coupling agent, in preferred embodiments, is a very thin monolayer of material. The length of the joint 50 can be varied from catheter to catheter. Variances in joint 50 design and length depend upon the desired application for the catheter 10, materials chosen for the proximal and distal regions, and overall length of the catheter as a whole.

In a preferred embodiment, the proximal segment 30 within the joint 50 is a tubular member, and more preferably, is a metallic hypotube. In certain embodiments, the hypotube originates from the catheter's manifold assembly 16. The hypotube then extends distally to a point within the intermediate segment 31 where the hypotube then terminates. In alternative embodiments, the proximal end of the hypotube originates distally from the catheter manifold assembly 16.

The second component of the joint 50 of FIG. 2 is a polymeric overlay portion of the intermediate segment 31. In preferred embodiments, a polymeric material is extruded over a portion of the metallic tubular member. The polymeric material is then further extruded to form a tubular member in the distal region of the catheter assembly 10. Polymeric material is extruded in a tubular configuration having a lumen defined therein. Alternatively, the tubular segment 31 may be preformed and assembled in overlapping fashion with the proximal segment 30.

Materials used to form the intermediate outer tubular member may vary depending on the stiffness or flexibility desired for the shaft assembly. Nylon and similar polyamides such as DURETHAN® (available from Bayer) are particularly suitable for rigid outer tubular members. Other suitable materials for a rigid outer tubular member include polyetheretherketone (PEEK), polyimide (PI), and polyetherimide (PEI). Polyether block amide (PEBA) is a relatively flexible polymeric material having a durometer of approximately 70 D which can also be utilized as a shaft material. Finally, the use of a polyamide such as CRISTAMID® (available from Elf Atochem) imparts a slightly less rigid durometer than the rigid polyamides and slightly greater than the PEBA material.

The portion of polymeric material extending over the metallic tubular member is a lap joint. A lap joint forms a continuous connection between a first segment and a second segment. By definition, however, the profile of a lap joint is not contiguous between the two segments. One segment is displaced over the second segment forming a portion of catheter assembly 10 having properties of both the first and second segments.

Referring now to FIGS. 3 and 4, a joint 60 depicting a bond between a metallic shaft segment, namely intermediate shaft segment 31 and a polymeric distal shaft segment 32 at the guidewire port 40 of the SOE catheter, is depicted in cross-sectional view. FIG. 4 further shows the cross section at line 4-4 of FIG. 3. As shown in FIG. 3, a distal portion of the intermediate shaft segment 31 extends within and is overlapped by the distal outer tubular segment 32. Further, the inner tubular member 33 overlaps the distal portion of the intermediate tubular segment 31. Thus, a bond is formed between the single proximal hypotube member and the two polymeric segments extending distally therefrom. In the embodiment shown in FIG. 3, the coupling agent is not shown as it would likely be a very thin layer or monolayer of material relative to the thicknesses of the tubular members. Alternatively, as discussed below, the coupling agents can be incorporated into the polymeric tubular members prior to extrusion.

Dissimilarities in material compositions of the two components of the joint generally require sufficient length for adequate strength in the resulting lap bond. Lap joint failure may result in the separation of the two component halves of the catheter shaft 10. Achieving a stronger bond between the two dissimilar materials allows shortening of the length of the bond. As such, an improved bond is desired in forming the lap joint.

Success in bonding a lap joint between a polymeric material and a stainless steel hypotube has been traditionally achieved using thermal bonding in combination with an adhesive. In these traditional methods, the adhesive is first applied between the two components. The two components are then thermally bonded together to form the completed lap joint. There exist drawbacks, however, to using adhesives in lap joint formation. Adhesives suitable for lap joints are commonly associated with long curing times, sensitivity to ambient conditions (including humidity and temperature), and the need for extensive surface treatment (generally including expensive plasma treatment systems). As a result, lap joints formed using adhesives are typically time and labor intensive. Further, the layer of adhesive fills a gap between the stainless steel hypotube and polymeric shaft and increases the profile of the resulting bonded shaft in the joint area.

Adhesives common in catheter manufacturing often take up to four hours to cure. In certain circumstances, a backfilling procedure may also be required. Backfilling over lap joints, on average, may add at least two additional hours to the overall curing time to the lap joint formation procedure. Moreover, procedures for lap joint formation are highly dependent on operator skill. Assemblers must initially apply the appropriate amount of adhesive between the lap joint to insure proper adhesion. The assembler must then sculpt a backfill onto the bond using additional adhesive to provide a smooth transition. Assembler errors and curing times may result in substantial delays. Delays in catheter production increase the manufacturer's costs.

The present invention identifies the use of coupling agents, alone and in conjunction with thermal bonding processes, to eliminate needless production delays that may result in increased consumer costs. Coupling agents are materials that improve the adhesive bonding characteristics between dissimilar surfaces. With respect to the present invention, the two dissimilar surfaces of particular concern are the stainless steel hypotube and the polymeric overlay portion or the shaft segment at joint 50 of catheter assembly 10.

A bond using a coupling agent as a primer generally requires little or no curing time. A coupling agent applied to a catheter segment may be immediately passed down the assembly line for assembly. Under preferred conditions, the cumulative throughput from priming to the final heat shrink removal may take less than ten minutes. Additionally, the use of coupling agents in the lap joint formation processes is substantially less operator dependent. Current technology provides machinery capable of streamlining the formation process from the initial application of the coupling agent to the laser weld that insures the strength of the final bond.

Coupling agents are compounds containing at least two sets of functional groups. A first set of functional groups has a bonding affinity with organic compounds. A second set of functional groups has a bonding affinity with inorganic compounds. For example, the first set of functional groups may bind with a polymeric material, whereas the second set of functional groups may bind with a metal. Preferred coupling agents possess first functional groups that form covalent bonds with a polymeric material, whereas the second set of functional groups of the same preferred coupling agent forms ionic bonds with a metal such as stainless steel Preferred coupling agents include functionalized titanates, functionalized aluminates, functionalized silanes and functionalized zirconates. In accordance with the general description of coupling agents described in detail above, these coupling agents have a first functional group and a second functional group corresponding to a bonding affinity with a polymer and a metal, respectively. In preferred embodiments, the functionalized coupling agents include a first functional group comprising hydrolyzable functional groups. In an alternative embodiment, the functionalized coupling agents include a second functional group comprising (meth)acrylate monomers. In yet another embodiment, the functionalized coupling agents include a second functional group comprising amine monomers.

A number of coupling agents suitable for medical device lap joint formation are commercially available. In a presently preferred embodiment, a series of functionalized titanates are used which are commercially available from Kenrich Petrochemicals, Inc., of Bayonne, N.J. under the tradename LICA. Functionalized titanates, neopentyl(diallyl)oxy,tri(diooctyl)pyro-phosphato titanate (tradename LICA 38), neopentyl(diallyl)oxy,tri(N-ethylenediamino) ethyl titanate (tradename LICA 44), and neopentyl(diallyl) oxy,tri(m-amino)phenyl titanate (tradename LICA 97) are particularly suitable for lap joints between stainless steel and polymeric materials. These coupling agents possess superior bonding affinities with both polymeric and stainless steel materials, with and without the use of thermal bonding and laser welding.

Coupling agents are commercially available in a variety of differing material states. For example, specific coupling agents are commercially available as powders, pastes and liquids. The use of one material state may be more appropriate than another depending upon the manner of manufacturing the medical device. Coupling agents in powder form are particularly suited for incorporation within a polymeric material, but can also be used separate from the polymer. The powdered coupling agent is measured, added and dispersed within the polymeric material to maintain a specified concentration throughout the mixture. The coupling agent polymer is then fed into an extruder. The extruder then dispenses the polymeric material so that it may overlay at least a portion of the hypotube, and furthermore, continue to form the remaining portions of the polymeric tubular member. Coupling agents in paste and liquid form are additionally suitable for this manufacturing method.

In alternative manufacturing techniques, the hypotube or polymeric tubular member may be primed with a thin layer of coupling agent. The applied "primer layer" is generally very thin, on the order of molecules of thickness. The primer layer is generally applied to the metallic or polymeric material by a dipping or a spraying process. Alternative methods of primer application, being known in the art, are also incorporated as within the spirit and scope of the present invention.

The use of certain coupling agents may require no further processing beyond application of the primer layer and the subsequent joining of the two dissimilar materials. In some embodiments, lap joints formed with these coupling agents can exceed the strength and durability requirements necessary for intravascular medical devices. Alternatively, other coupling agents require further processing in order to achieve the desired strength requirements. Likewise, coupling agents that do not require further processing can be further aided by such additional processing. Thermal bonding techniques can aid in lap joint formation using coupling agents. The following example of a lap joint formation process for an intravascular catheter is presented by way of illustration, and not by way of limitation:

The bonding site on a stainless steel hypotube is cleaned and polished using a very fine sandpaper. The bonding site is then washed using detergent and water to remove any remaining residual debris from the hypotube. The cleaned parts are then placed into a 65 degree Centigrade oven until dried. A 1% solution of neopentyl(diallyl)oxy, tri(N-ethylenediamino) ethyl titanate (tradename LICA 44 from Kenrich Petrochemicals, Inc., of Bayonne, N.J.) is then brushed over the bonding site on the hypotube's surface. The hypotube is then again placed within the 65 degree Centigrade oven for 30 minutes to dry the bonding site surface. The dried hypotube is then washed twice and dried. A portion of a polymeric tubular member is then disposed over the bonding site. The bonding site is then placed within a thermal bonding machine that subjects the bonding site, in particular, to a temperature of 400 degrees Fahrenheit for 30 seconds to form the lap joint.

Although the use of coupling agents to this point has focused primarily on improving the adhesion between a stainless steel hypotube and an overlaid polymeric material of a catheter, coupling agents may additionally be used to increase adhesion of other medical device components having a polymeric material overlaying a metallic surface. More specifically, often the metallic framework of stents is coated with a polymeric material. Polymeric materials are excellent carrier mediums for therapeutic substances. Various polymers may be utilized that are bioresorbable at specific rates. Combining these polymers with therapeutic substances allows for prolonged treatment of a localized area deep within the tortuous vasculature of a patient. As with the formation of lap joints, the polymeric material often resists attachment to the metallic framework of the stent. Therefore, it is believed that priming either of the dissimilar surfaces with a coupling agent may enhance the resulting bond between the metal framework of the stent and the polymeric overlay.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is of course defined in the language in which the appended claims are expressed.

What is claimed is:

1. In a catheter having a lap joint between a metallic tubular member and a polymeric tubular member, the improvement in the catheter comprising:
   a coupling agent, wherein the coupling agent is disposed between the metallic tubular member and the polymeric tubular member in the lap joint, the coupling agent having a first functional group and second functional group, the first functional group providing bonding adhesion to the metallic tubular member, the second functional group providing bonding adhesion to the polymeric tubular member, wherein the coupling agent maintains bonding adhesion between the metallic tubular member and the polymeric tubular member when in use, wherein the coupling agent is a functionalized titanate.

2. The improvement of claim 1, wherein the first functional group of the coupling agent comprises at least one hydrolyzable functional group.

3. The improvement of claim 2, wherein the second functional group of the coupling agent comprises at least one (meth)acrylate monomer.

4. The improvement of claim 1, wherein the second functional group of the coupling agent comprises of at least one amine monomer.

5. The improvement of claim 1, wherein the functionalized titanate is neopentyl(diallyl)oxy,tri(dioctyl)pyro-phosphato titanate.

6. The improvement of claim 1, wherein the functionalized titanate is neopentyl(diallyl)oxy,tri(N-ethylenediamino) ethyl titanate.

7. The improvement of claim 1, wherein the functionalized titanate is neopentyl(diallyl)oxy,tri(m-amino)phenyl titanate.

* * * * *